US010653387B2

(12) United States Patent
Tanter et al.

(10) Patent No.: US 10,653,387 B2
(45) Date of Patent: May 19, 2020

(54) METHOD AND DEVICE FOR FUNCTIONAL IMAGING OF THE BRAIN (71) Applicants: CENTRE NATIONAL DE LA RECHERCHE SCIENTIFIQUE—CNRS, Paris (FR); INSERM (INSTITUT NATIONAL DE LA SANTÉ ET DE LA RECHERCHE MÉDICALE), Paris (FR); ECOLE SUPERIEURE DE PHYSIQUE ET DE CHIMIE INDUSTRIELLES DE LA VILLE DE PARIS, Paris (FR); Université Pierre et Marie Curie (Paris 6), Paris (FR); Université Paris Diderot—Paris 7, Paris (FR)

(72) Inventors: Mickaél Tanter, Bagneux (FR); Jean-luc Gennisson, Cergy (FR); Thomas Deffieux, Kremlin Bicetre (FR); Mathieu Pernot, Parid (FR)

(73) Assignees: INSTITUT NATIONAL DE LA SANTÉ ET DE LA RECHERCHE MÉDICALE (INSERM), Paris (FR); CENTRE NATIONAL DE LA RECHERCHE SCIENTIFIQUE (CNRS), Paris (FR); ÉCOLE SUPERIEURE DE PHYSIQUE ET DE CHIMIE INDUSTRIELLES DE LA VILLE DE PARIS, Paris (FR); UNIVERSITÉ PIERRE ET MARIE CURIE (PARIS 6), Paris (FR); UNIVERSITÉ PARIS DIDEROT—PARIS 7, Paris (FR)

( * ) Notice: Subject to any disclaimer, the term of this patent is extended or adjusted under 35 U.S.C. 154(b) by 307 days.

(21) Appl. No.: 15/323,305

(22) PCT Filed: Jun. 29, 2015

(86) PCT No.: PCT/FR2015/051752
§ 371 (c)(1),
(2) Date: Dec. 30, 2016

(87) PCT Pub. No.: WO2016/001548
PCT Pub. Date: Jan. 7, 2016

(65) Prior Publication Data
US 2017/0128036 A1 May 11, 2017

(30) Foreign Application Priority Data
Jul. 2, 2014 (FR) ..................... 14 56301

(51) Int. Cl.
*A61B 8/06* (2006.01)
*G06T 7/174* (2017.01)
(Continued)

(52) U.S. Cl.
CPC .............. *A61B 8/06* (2013.01); *A61B 8/0808* (2013.01); *A61B 8/483* (2013.01); *A61B 8/488* (2013.01);
(Continued)

(58) Field of Classification Search
CPC ......... A61B 8/06; A61B 8/0808; A61B 8/483; A61B 8/488; A61B 8/5223; A61B 8/5246;
(Continued)

(56) References Cited
U.S. PATENT DOCUMENTS 7,037,267 B1 * 5/2006 Lipson ................. A61B 5/6834
600/437
7,072,705 B2 * 7/2006 Miga .................. G06K 9/00214
600/411
(Continued)

FOREIGN PATENT DOCUMENTS

JP 2008229334 A 10/2008

OTHER PUBLICATIONS

Macé, "Functional ultrasound imaging of the brain", Nature Methods, vol. 8, No. 8, pp. 662-666 (Year: 2011).*

(Continued)

*Primary Examiner* — Joanne M Hoffman
(74) *Attorney, Agent, or Firm* — W&C IP

(57) ABSTRACT

Method for functional imaging of the brain, comprising the following steps: (a) a brain is imaged by ultrasound imaging in order to obtain a vascular image to be studied (IVO), (b) the vascular image to be studied (IVO) is compared automatically, by shape recognition, with a cerebral vascular atlas (AV), and the vascular image to be studied (IVO) is thus located in the cerebral vascular atlas (AV), (c) a cerebral functional atlas (AF) corresponding to said cerebral vascular atlas (AV) and comprising cerebral functional zones ($1c$) located in this cerebral vascular atlas (AV) is used in such a way as to identify cerebral functional zones ($1e$) on the vascular image to be studied (IVO).

17 Claims, 5 Drawing Sheets

(51) Int. Cl.
| | |
|---|---|
| *A61B 8/08* | (2006.01) |
| *G06T 7/149* | (2017.01) |
| *G06T 7/12* | (2017.01) |
| *G06T 7/00* | (2017.01) |

(52) U.S. Cl.
CPC .......... *A61B 8/5223* (2013.01); *A61B 8/5246* (2013.01); *G06T 7/0016* (2013.01); *G06T 7/12* (2017.01); *G06T 7/149* (2017.01); *G06T 7/174* (2017.01); *A61B 8/0891* (2013.01); *A61B 8/523* (2013.01); *G06T 2207/10072* (2013.01); *G06T 2207/10136* (2013.01); *G06T 2207/20128* (2013.01); *G06T 2207/30016* (2013.01); *G06T 2207/30104* (2013.01)

(58) Field of Classification Search
CPC .......... G06T 7/12; G06T 7/149; G06T 7/174; G06T 7/0016
See application file for complete search history.

(56) References Cited

U.S. PATENT DOCUMENTS

| | | | |
|---|---|---|---|
| 8,233,681 B2* | 7/2012 | Aylward | A61B 90/36 |
| | | | 382/128 |
| 2008/0275340 A1 | 11/2008 | Beach et al. | |
| 2009/0270790 A1* | 10/2009 | Raghavan | A61M 37/00 |
| | | | 604/22 |
| 2010/0143241 A1* | 6/2010 | Johnson | A61K 41/0028 |
| | | | 424/1.11 |
| 2013/0131495 A1 | 5/2013 | Konofagou et al. | |
| 2015/0119689 A1* | 4/2015 | Pascual-Leone | A61N 2/006 |
| | | | 600/410 |
| 2017/0065176 A1* | 3/2017 | Steinle | B29C 64/386 |
| 2018/0042544 A1* | 2/2018 | Graham | A61B 5/16 |

OTHER PUBLICATIONS

Du, "Atlas Image Labeling of Subcortical Structures and Vascular Territories in Brain CT images", 35th Annual International Conference of the IEEE EMBS, pp. 6530-6534 (Year: 2013).*
Macé, "Functional ultrasound imaging of the brain: theory and basic principles", IEEE Trans Ultrason Ferroelectr Freq Control. Mar. 2013;60(3):492-506. (Year: 2013).*
Macé, "Functional ultrasound imaging of the brain", Nature Methods, vol. 8, No. 8, (supplemental drawings) (Year: 2011).*
Brain CT images, 35th Annual International Conference of the IEEE EMBS, pp. 6530-6534 (Supplementary Software) (Year: 2013).*
Macé, "Functional ultrasound imaging of the brain", Nature Methods, vol. 8, No. 8, pp. 662-666 with supplemental areas shown in PDF (Year: 2011).*
Emilie Mace et al: "Functional ultrasound imaging of the brain", Nature Methods, vol. 8, No. 8, Jan. 2, 2011, pp. 662-664.
Martijn E Van Raaij et al: "Functional micro-ultrasound imaging of rodent cerebral hemadynamics", Ultrasonics Symposium (IUS), 2011 IEEE International, IEEE, Oct. 18, 2011, pp. 1258-1261.
Pennec X et al: "Tracking brain deformations in time sequences of 3d us images", Pattern Recognition Letter, Elsevier, Amsterdam, NL, vol. 24, No. 4-5, Feb. 2, 2003, pp. 801-813.

* cited by examiner

METHOD AND DEVICE FOR FUNCTIONAL IMAGING OF THE BRAIN

FIELD OF THE INVENTION

The present invention relates to method and devices for functional imaging of the brain.

BACKGROUND OF THE INVENTION

Brain functional imaging consists of imaging the transient changes of an area of the brain related to a neuronal activity, in animals or in humans. The areas of the brain corresponding to different specific functions (for example displacement of certain limbs, the use of certain sensorial detectors, emotions, memory, etc) are listed in known functional anatomic atlases, respectively corresponding to various animal species or to human beings (for example the "Paxinos" atlases), and brain functional imaging gives the possibility of locating and measuring the neuronal activity in certain of these functional areas, matching with a certain activity of the human or the animal on which is practiced functional imaging.

Certain brain functional imaging techniques are based on the measurement of electric currents (EEG) or magnetic fields (MEG) generated by the neurones. These techniques have a very limited spatial resolution because of the complexity of the inverse problem to be solved for again finding the position of the electric activity sources.

The other techniques giving the possibility of imaging these functional changes are based on the neuro-vascular coupling: when the neurones have strong activity in an area of the brain, a supply of glucose is required in this area. For this, the vascular flow increases in this specific area. By imaging the vascular flows in the brain, it is possible to infer therefrom which are the functional areas activated in the functional atlas of the human or the animal, the brain of which is imaged.

Several techniques may be used for imaging these changes in blood flow:
  functional MRI (also called "MRIf") which images the change in oxygenation related to a change in blood flow,
  nuclear imaging (PET) which images the binding of glucose brought by the blood flow,
  and the ultrasonic functional imaging.

In fMRI, the localization of the activated functional area is easily accomplished, since the MRI images are of very good quality and give the possibility of quite easily locating the anatomy and therefore the activated functional area of the brain. The functional imaging is then carried out and superimposed to an anatomic image produced by the MRIf machine before acquiring the functional image. This technology however has many drawbacks: the fMRI machines are very costly and cumbersome, and only provide a good spatial resolution with the expense of a significant reduction of the time resolution, which does not give the possibility of imaging transient phenomena in the brain (epilepsy fit for example).

PET has very poor spatial resolution. It gives an interesting functional piece of information, but once the activated area has been located, it is not possible to know to which anatomic or functional area of the brain it corresponds, so that it is necessary to combine a PET imaging machine with an MRI machine or a CT scanner in order to obtain a useable result. Such an imaging assembly is however extremely expensive.

The ultrasonic functional imaging is based on ultrasensitive imaging of the blood flow (Mace et al, "Functional ultrasound imaging of the brain: theory and basic principle", IEEE Trans Ultrasonic Ferroelectric Freq. Control. 2013 March; 60(3): 492-506), for which the variation overtime gives access to the activated functional areas (Mace et al, "Functional ultrasound imaging of the brain", Nature Methods, 8, 662-664, 2011).

Ultrasonic functional imaging gives the possibility of obtaining at a relatively low cost, an extremely accurate vascular image of the brain and the localization of the activated areas on this vascular image. A difficulty is however to be able to have the vascular image correspond with an anatomic image giving the possibility of locating the functional areas. Indeed, the anatomic image which may be acquired in echography by the ultrasonic functional imaging device, is of too low quality for allowing localization of the imaged functional areas.

Consequently, only an expert operator is capable of localizing the functional areas imaged in ultrasonic functional imaging: he/she has to locate with the naked eye in the vascular image, global structures of the brain which will allow him/her to position the image in the brain, and then attempt to find where is located the functional area which is of interest to him/her by organ of an atlas.

SUMMARY OF THE INVENTION

The present invention notably has the object of overcoming these drawbacks.

For this purpose, the invention proposes a functional imaging method of the brain by ultrasonic waves, comprising the following steps:
  (a) a vascular imaging step during which a brain of a human or animal subject is imaged by ultrasonic imaging, in order to obtain a vascular image to be studied, said subject belonging to a certain class of subjects,
  (b) a localization step, during which, by shape recognition, at least one portion of the vascular image to be studied is automatically compared with a brain vascular atlas corresponding to said class of subjects, and the vascular image to be studied is thereby located in the brain vascular atlas,
  (c) an identification step during which a brain function atlas is used corresponding to said brain vascular atlas and comprising brain functional areas located in this brain vascular atlas, so that at least one brain functional area is identified on the vascular image to be studied.

The aforementioned atlases (brain functional atlas matching with the brain vascular atlas) thereby allow automatic localization, by shape recognition, what are the visible brain functional areas on the vascular image to be studied. The identification of the functional areas of the brain, viewed, may thus be carried out easily and rapidly, even by a non-expert user. The functional and vascular atlases corresponding to different classes of subjects, may be produced in advance and available in a library of atlases stored on a computer. A class of subjects may for example match one or several criteria notably selected from among: species, gender, age, weight.

In diverse embodiments of the method according to the invention, it is optionally possible to resort further to either one or both of the following provisions:
  during the localization step (b), a portion of the brain vascular atlas is matched with the vascular image to be studied, and during the identification step, a map of functional areas corresponding to said portion of the brain vascular atlas is determined, and the vascular image to be studied is superposed with said map of functional areas;

during the localization step, a geometrical deformation is determined giving the possibility of passing from said at least one portion of the brain vascular atlas to the vascular image to be studied, and during the identification step, the functional map of the vascular image to be studied is determined by applying this geometrical deformation to a portion of the brain functional atlas corresponding to said portion of the brain vascular atlas which corresponds to the vascular image to be studied;

in the localization step (b), said shape recognition is carried out by correlation between the vascular image to be studied and the brain vascular atlas;

the vascular image to be studied is representative of the blood flows in at least one portion of the brain;

the vascular image to be studied includes at least one piece of hemodynamic information selected from among: the brain vascular volume (cf (Mace et al, "Functional ultrasound imaging of the brain: theory and basic principle", IEEE Trans Ultrasonic Ferroelectric Freq. Control. 2013 March; 60(3): 492-506), the Doppler power, the blood flow speed, the Doppler color, a representative value of the circulation resistance (Pourcelot index or other);

the reference functional vascular mapping is a three-dimensional mapping; for example, it may comprise a plurality of brain sections in successive planes;

the brain vascular atlas contains data stemming from imaging selected from among: ultrasonic imaging, angioscanner, MRI, CT scanner;

the method further comprises, between the imaging step (a) and the localization step (b), a preliminary localization step (b0) during which at least one characteristic area normally present in any subject to be studied and in the brain vascular atlas is automatically detected on the vascular image to be studied, and the vascular image to be studied is thereby located in the brain vascular atlas;

said characteristic area is selected from among: the Willis polygon, Sylvian veins, the anterior brain artery, the greatest arteries of the brain;

the method includes at least one preliminary step (p) for the reference functional vascular mapping, comprising the following sub-steps:

(p1) a reference imaging sub-step during which are produced both:

said brain vascular atlas of at least one subject from the class of considered subjects, and an anatomic reference atlas made by imaging the brain of said at least one subject from the considered class of subject, by a second type of imaging giving an anatomic image of the brain which is more accurate than the ultrasonic imaging, (p2) a reference functional mapping sub-step during which said brain functional atlas is determined from a functional anatomic atlas which comprises at least one typical anatomic atlas of the brain and the functional areas located on this typical anatomic atlas, this reference functional mapping sub-step being carried out by matching said reference anatomic atlas with the typical anatomic atlas for locating the functional areas of the functional anatomic atlas on said brain vascular atlas;

during the sub-step (p1) for the reference imaging, said brain vascular atlas is produced by vascular ultrasonic imaging of the brain:

during the reference functional mapping sub-step (p2), the reference anatomic atlas is matched with the typical anatomic atlas by shape recognition;

during the sub-step (p2) of reference mapping, a geometrical deformation is determined giving the possibility of passing from said reference anatomic atlas to the typical anatomic atlas, this geometrical deformation is applied to the brain vascular atlas and the brain vascular atlas is thus matched with the functional areas of the functional anatomic atlas;

during said reference imaging sub-step (p1), several vascular initial images are successively produced on several subjects of the class of considered subjects, by vascular ultrasonic imaging of the brain and several initial anatomic images by said second type of imaging, and said brain vascular atlas is determined and said reference anatomic atlas are determined by a statistical calculation respectively from said initial vascular images and from initial anatomic images;

each initial vascular image is three-dimensional;

each initial vascular image is two-dimensional, the reference functional vascular mapping being obtained from reference vascular images produced along a plurality of successive planes;

each class of subject corresponds to at least one criterion selected from among: species, gender, age, weight;

a stimulus is applied to the subject and on the brain vascular image (IV0) an activation of at least one frequency area (1c) subsequent to this stimulus is detected;

on the brain vascular image, an action targeted towards at least one identified functional area on the brain vascular image is viewed, and this action is guided towards said second identified functional area;

said action is selected from an electrode implantation, a fluid injection, a remote stimulation with a wave (electromagnetic, sound, ultrasonic, light wave);

the imaging step is carried out with at least one ultrasonic probe which may be moved with motor-driven organ, and said at least one probe is displaced until the brain vascular image corresponds to at least one desired functional area;

the imaging step (a) is achieved with at least one adapted ultrasonic probe for producing a three-dimensional image, and a two-dimensional image is extracted from said three-dimensional image which matches at least one desired functional area.

Moreover, the object of the invention is also a device for applying a method as defined above, comprising:

vascular imaging organ adapted for imaging a brain of a human or animal subject by ultrasonic imaging, in order to obtain a vascular image to be studied, said subject belonging to a certain class of subjects, organ for localization by shape recognition, adapted for automatically comparing the vascular image to be studied, with a reference functional vascular mapping corresponding to said class of subjects, said reference functional vascular mapping comprising a typical brain vascular network for which said class of subjects and of the brain functional areas corresponding to this typical brain vascular network, said localization organ being adapted for determining, in this way which brain functional areas from the reference functional vascular mapping correspond to the vascular image to be studied.

SHORT DESCRIPTION OF THE DRAWINGS

Other features and advantages of the invention will become apparent during the following description of one of its embodiments, given as a non-limiting example, with reference to the appended drawings.

In the drawings.

DETAILED DESCRIPTION

In the different figures, the same references designate identical or similar elements.

Figure 1:
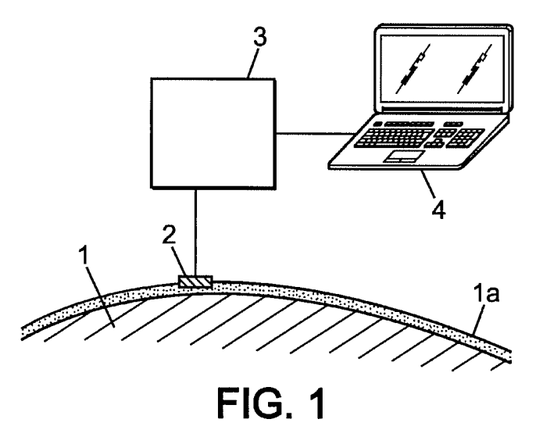
FIG. 1 is a schematic view of a device for applying a method according to an embodiment of the invention.

FIG. 1 shows an example of a device adapted for producing a vascular imaging of the brain 1 of a human or animal subject to be studied, by emission and reception of ultrasonic compressional waves, for example with frequencies comprised between 1 and 40 MHz. The emission and reception of ultrasonic waves may be accomplished by organ of a network 2 of ultrasonic transducers either by crossing all or part of the brain 1a of the subject, or directly upon contacting the brain 1, notably at one or several trepanations of the brain 1a.

Figure 2:
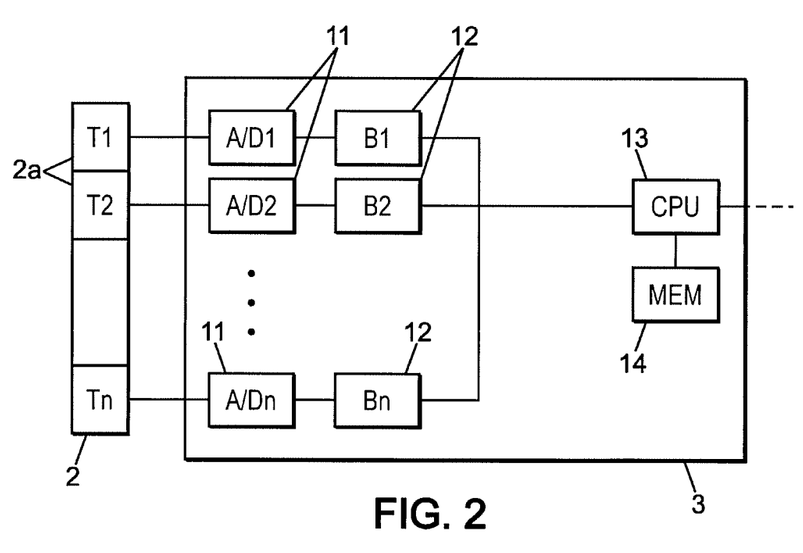
FIG. 2 is a block diagram of a portion of the device of FIG. 1.

The imaging device for example includes, as illustrated in FIGS. 1 and 2:
  a network 2 of n ultrasonic transducers $2a$ ($T_1$-$T_n$), for example comprising a few hundred transducers $2a$, this network 2 may for example be a bar of transducers (network 1D) suitable for producing a two-dimensional image (2D) or further a two-dimensional network adapted for producing a three-dimensional (3D) image;
  an electronic circuit 3 controlling the network of transducers 2 and adapted for emitting ultrasonic waves with the network of transducers and acquiring the signals captured by this network of transducers;
  a computer 4 or similar device for controlling the electronic circuit 3 and viewing the ultrasonic waves obtained from said captured signals.

As illustrated in FIG. 2, the electronic circuit 3 may for example comprise:
  n analog/digital converters 11 ($A/D_I$) individually connected to n transducers $T_1$-$T_N$ of the network 2 of transducers,
  n buffer memories 12 ($B_I$) respectively connected to the n analog/digital converters 11,
  a central processing unit 13 (CPU) communicating with the buffer memories 12 and the computer 4 and adapted to the processing of the signals sent towards the network of transducers 2 and received from said network of transducers,
  a memory 14 (MEM) connected to the central processing unit 13.

The imaging device illustrated in FIGS. 1 and 2 is adapted for producing synthetic ultrasonic imaging of the brain giving the possibility of finally imaging the brain vascular network and of giving at least one piece of hemodynamic information (i.e. relative to the blood flows), as notably described by Mace et al. (aforementioned publications "Functional ultrasound imaging of the brain: theory and basic principle", IEEE Trans Ultrasonic Ferroelectric Freq. Control. 2013 March; 60(3): 492-506) and "Functional ultrasound imaging of the brain", Nature Methods, 8, 662-664, 2011) and in document EP 2 101 191.

The piece of hemodynamic information given by the thereby obtained brain vascular image may notably be selected from among: the brain vascular volume, the Doppler power, the blood flow velocity, the Doppler color, a representative value of the circulation resistance (Pourcelot index or other).

Figure 3:
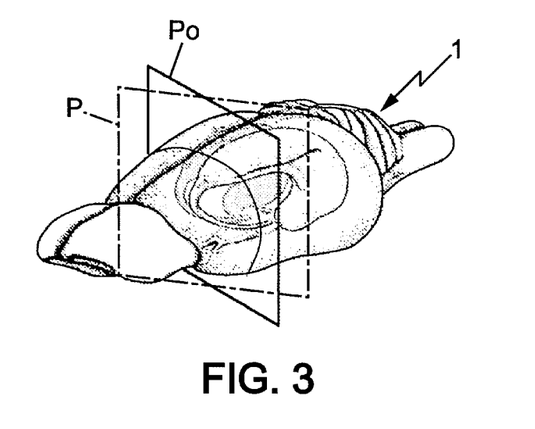
FIG. 3 is a perspective view of a rat brain showing an imaging plane in the case of two-dimensional imaging and a reference coronal plane.
Figure 4:
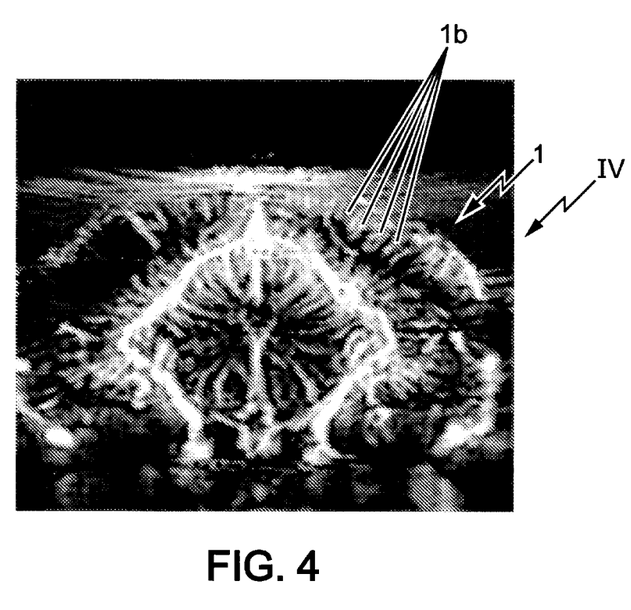
FIG. 4 is an example of a vascular image to be studied which may be produced by the ultrasonic imaging for example from the brain of FIG. 3, in a coronal plane.

As illustrated in FIG. 3, in the case of two-dimensional imaging, the brain vascular image may be produced in a plane P, for example with a direction close to a coronal plane P0 but in practice most often different from the perfect coronal plane P0. The obtained brain vascular image IV, visible in FIG. 4, gives the possibility of viewing the blood vessels 1b of the brain 1 with excellent definition, giving the possibility of viewing them including the microvessels. The aforementioned piece of hemodynamic information may be given by the light intensity of each pixel and/or by a color scale.

Figure 5:
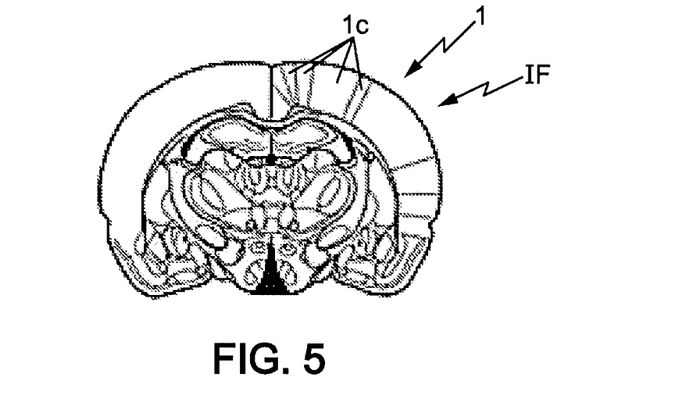
FIG. 5 is an example of a brain functional map which may for example match the brain of FIG. 3, in a coronal plane.

This piece of hemodynamic information reflects the local brain activity and therefore allows the accomplishment of functional imaging, provided that it is possible to locate each pixel of the image in a functional anatomic atlas of the brain (Paxinos or other) a coronal section IF of which is illustrated as an example in FIG. 5. Such a functional anatomic atlas contains a typical anatomic atlas of the brain (shape of the cerebral tissues) and a typical functional atlas consisting of functional areas 1c located on this typical anatomic atlas. Each of the functional areas 1c of the typical functional atlas corresponds to a motor-driven, sensitive or specific cognitive function and bears a determined reference corresponding to this function. Each functional anatomic atlas is valid for a class of studied subjects, for example corresponding to a species, to a gender (male/female), a range of weight and an interval of age of the studied subject (or only certain of these criteria, plus other ones optionally).

It is however very difficult for an operator to locate the brain vascular image IV in the functional anatomic atlas, since, on the one hand, the brain vascular image IV does not correspond to the anatomic images which may be extracted from the typical anatomic atlas and on the other hand, the plane P of the brain vascular image is generally not exactly a coronal plane P0 as explained above.

In order to find a remedy to this drawback, the invention provides the production in advance, for at least certain classes of subjects to be studied, a typical brain vascular atlas VA corresponding to said class of subjects, matching a typical brain functional atlas FA corresponding to said brain vascular atlas VA and for which the brain functional areas 1c are located in this brain vascular atlas (VA).

Both of these atlases may be established beforehand notably during a preliminary step (p) of reference functional vascular mapping, comprising the following sub-steps:

(p1) a reference imaging sub-step during which are produced:
said brain vascular atlas (produced by ultrasonic vascular imaging of the brain, or further by an angioscanner, MRI, CT scanner) of at least one subject from the considered class of subjects,
and an anatomic reference atlas produced by imaging the brain of said at least one subject from the considered class of subjects, by a second type of imaging giving a more accurate anatomic image of the brain than the ultrasonic imaging, for example by MRI, (p2) a sub-step for reference functional mapping during which said brain functional atlas is determined from a functional anatomic atlas (Paxinos or other) which comprises at least one typical anatomic atlas of the brain and of the located functional areas on this typical anatomic atlas, this reference functional mapping sub-step being achieved by having said reference anatomic atlas match the typical anatomic atlas, for locating the functional areas of the functional anatomic atlas on said brain vascular atlas.

Figure 6:
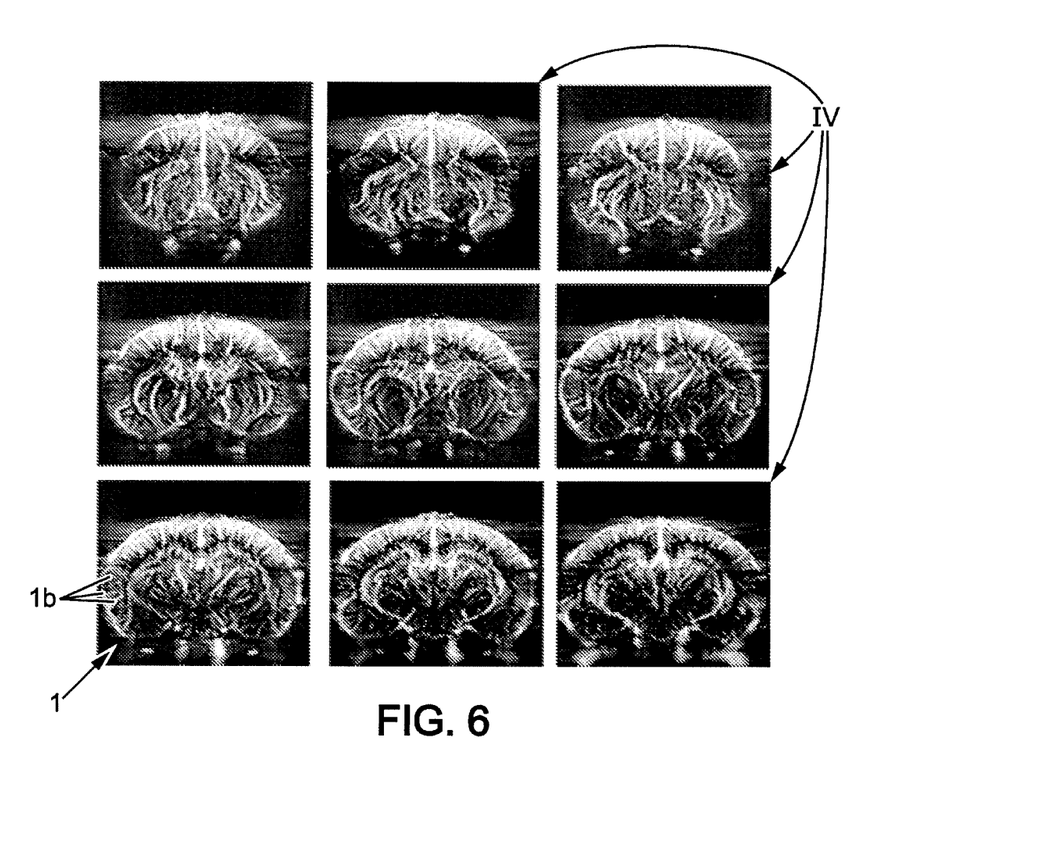
FIG. 6 shows an assembly of initial vascular images taken in successive coronal planes of a rat brain with view to participating in the making up of a brain vascular atlas of a certain class of rats.
Figure 7:
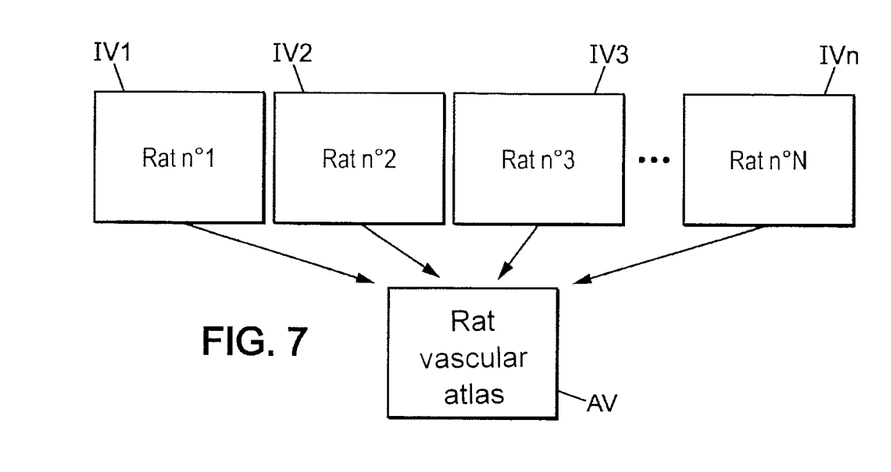
FIG. 7 schematically illustrates the production of said brain vascular atlas.

During said reference imaging sub-step (p1), it is possible to successively produce on several subjects of the class of considered subjects, respectively several initial vascular images VI (FIG. 6) by vascular ultrasonic imaging of the brain and several initial anatomic images by said second imaging type. Said brain vascular atlas and said reference anatomic atlas are determined by a statistical calculation respectively from said initial vascular images and initial anatomic images (for example, respectively by the average of said initial vascular images and of the initial anatomic images), as schematically illustrated in FIG. 7 for the brain vascular atlas in rats.

During the reference functional mapping sub-step (p2), it is possible to match the reference anatomic atlas with the typical anatomic atlas by shape recognition. For example, a geometrical deformation is determined, giving the possibility of passing from said reference anatomic atlas to the typical anatomic atlas, and then this geometrical deformation is applied to the brain vascular atlas and thus the brain vascular atlas is matched with the functional areas of the functional anatomic atlas.

Figure 8:
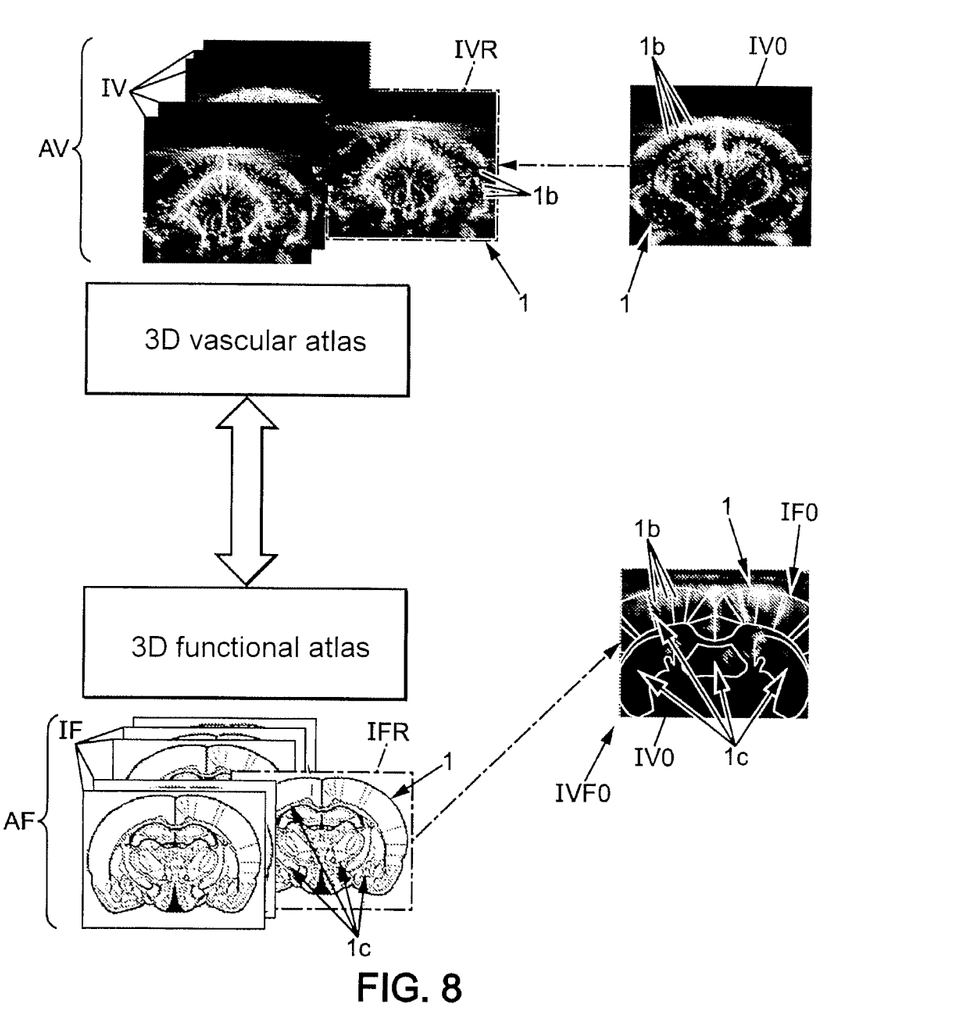
FIG. 8 schematically illustrates the production of a coronal brain vascular image incorporating a functional map according to the invention, by using the sole ultrasonic imaging.

Once it is established that the typical brain vascular atlas VA corresponding to a class of subjects, is matched with the typical brain functional atlas FA for the same class of subjects, it is possible to easily and automatically locate the functional areas on a brain vascular image VI0 exclusively produced by ultrasonic imaging, by the process illustrated in FIG. 8:

(a) Imaging:
A brain 1 of the subject is imaged by ultrasonic imaging, in order to obtain the vascular image to be studied VI0.

(b0) Optional preliminary localization:
Optionally, a rough preliminary localization is first carried out during which at least one characteristic area normally present in any subject to be studied and in the brain vascular atlas VA is detected automatically. Said characteristic area may be a point or an invariant structure of the brain, for example, the Willis polygon, the Sylvian veins, the anterior brain artery, the largest arteries of the brain.

(b) Localization:
By shape recognition, the vascular image to be studied VI0 is automatically compared by correlation with the brain vascular atlas VA corresponding to the class of subjects to which belongs the studied subject, and the vascular image to be studied VI0 is thereby located in the brain vascular atlas VA. In practice, this step for localizing the vascular image to be studied VI0 in the vascular atlas VA is accomplished by determining by shape recognition, a vascular image VIR stemming from the vascular atlas VA, corresponding at best to the vascular image to be studied VI0. The vascular atlas VA may optionally be formed by a series of two-dimensional brain vascular image series VI taken in successive adjacent planes (for example coronal planes, or other ones), and the aforementioned localization may consist, in a simplified version, in selecting the brain vascular image VIR closest to the vascular image to be studied VI0 (which, in this case, is a two-dimensional image). In a more elaborate version and when the vascular image to be studied VI0 is two-dimensional, this localization also consists in determining by shape recognition, the orientation and the position of the plane of the image VI0, and of reconstructing an image VIR from the vascular atlas VA in this plane (whether the atlas is three-dimensional or formed by a series of two-dimensional brain vascular images VI taken in successive adjacent planes).

(c) Identification:
By organ of the brain functional atlas FA corresponding to said brain vascular atlas VA, at least one brain functional area 1c is identified on the vascular image to be studied VI0. More specifically, an image IFR stemming from the functional atlas FA, corresponding to the aforementioned VIR, is determined and this image IFR is matched with the vascular image to be studied VI0, by geometrical deformation, in order to thereby determine a functional map FI0 (formed by the limits of the functional areas 1c), which are superposed to the vascular image to be studied VI0 in order to thereby obtain a functional vascular image FVI0 of the brain 1.

More specifically, during the localization step (b), it is possible to determine a geometrical deformation giving the possibility of passing from the image VIR to the vascular image to be studied VI0, and during the identification step (c), it is possible to determine the functional map FI0 of the vascular image to be studied VI0 by applying this geometrical deformation to the image FIR stemming from the brain functional atlas FA.

Figure 9:
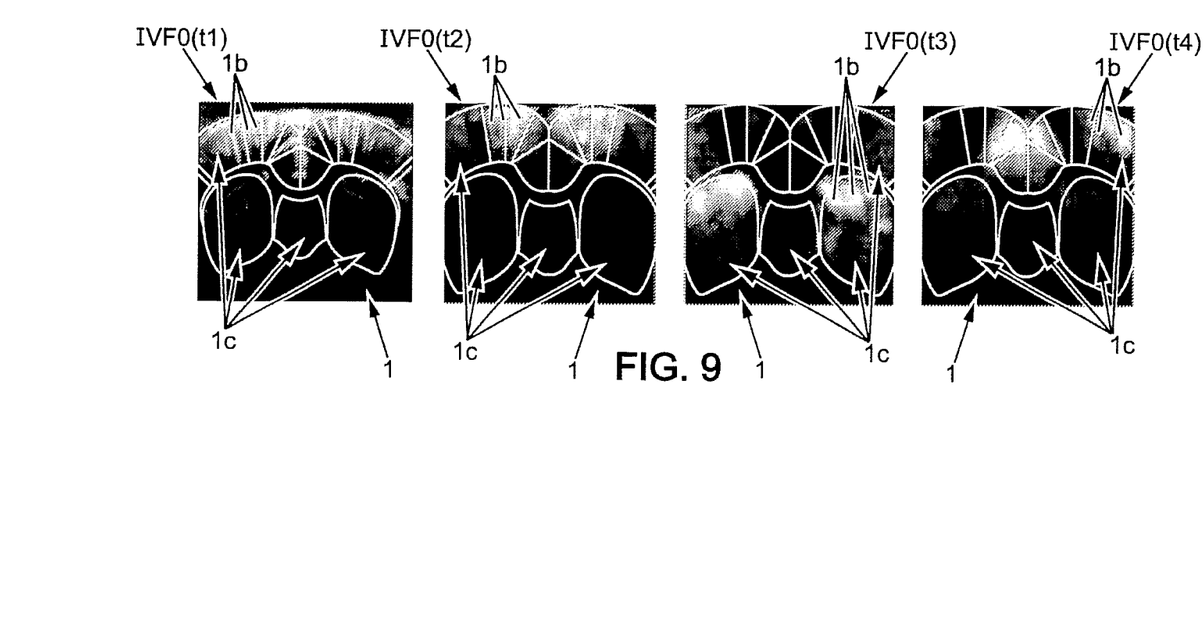
FIG. 9 shows an example of successive functional vascular images obtained by the method of the invention, giving the possibility of tracking in real time the activation of certain functional areas of the brain.

Once the functional map FI0 is established, it remains unchanged as long as the ultrasonic imaging probe 2 remains immobile (this probe may for example be rigidly attached to the brain 1a of the subject, or via a motor-driven actuator giving the possibility of controlling control displacements of this probe). It is then possible to produce brain vascular images VI0 overtime (see FIG. 9), for example synchronized with external or internal stimulations applied to the subject to be studied (including conscious or unconscious brain activity). These brain vascular images are superposed to the functional map FI0, so as to view and optionally record the activation of the functional areas 1c over time.

It is thereby possible to also view and guide the implantation of electrodes or the injection of particular therapeutic agents to the targeted functional areas, or further a remote stimulation with a wave (electromagnetic, ultrasonic, sound or light wave).

It will also be noted that the method described above easily gives the possibility of displacing the ultrasonic probe 2 to a desired position in order to image certain defined functional areas, when said probe 2 is rigidly attached to the brain 1a of the subject, or via a motor-driven actuator giving the possibility of controlling control displacements of this probe. Indeed, as the brain vascular image VI0 is located in the functional atlas FA, it is easy to determine the required displacement for viewing a desired functional area 1c.

Also, when the ultrasonic imaging is carried out with at least one ultrasonic probe 2 adapted for producing a three-dimensional image, it is possible to extract from this three-dimensional image, a two-dimensional image corresponding to at least one desired functional area 1c.

The invention claimed is:

1. A method for functional imaging of the brain by ultrasonic waves, comprising the following steps:
   an atlas producing step during which a brain vascular atlas and a brain functional atlas are produced by
      using at least one imaging technique to produce the brain vascular atlas of at least one subject from a certain class of subjects to be considered,
      using a second type of imaging on the brain of the at least one subject giving a more accurate anatomic image of the brain than ultrasonic imaging to produce a reference anatomic atlas,
      producing the brain functional atlas by matching the reference anatomic atlas with a functional anatomic atlas comprising a typical anatomic atlas having functional areas located on this typical anatomic atlas in order to locate the functional areas of the functional anatomic atlas on said brain vascular atlas,
   a vascular imaging step during which a brain of a human or animal subject is imaged by ultrasonic imaging, in order to obtain a vascular image to be studied from which one or more of blood vessels and microvessels are viewable, said subject belonging to the certain class of subjects,
   a localization step, during which, by shape recognition, at least one portion of the vascular image to be studied is automatically compared with at least one portion of the brain vascular atlas corresponding to said class of subjects, and the vascular image to be studied is thereby located in the brain vascular atlas,
   an identification step during which the brain functional atlas corresponding to said brain vascular atlas and comprising the functional areas located in this brain vascular atlas is used, wherein a map of functional areas corresponding to said portion of the brain vascular atlas is determined, and the vascular image to be studied is superposed with said map of functional areas so that at least one brain functional area is identified on the vascular image to be studied.

2. The method according to claim 1, wherein, during the localization step, a geometrical deformation is determined giving the possibility of passing from said at least one portion of the brain vascular atlas to the vascular image to be studied, and during the identification step, the functional map of the vascular image to be studied is determined by applying this geometrical deformation to a portion of the brain functional atlas corresponding to said portion of the brain vascular atlas which corresponds to the vascular image to be studied.

3. The method according to claim 1, wherein in the localization step, said shape recognition is carried out by correlation between the vascular image to be studied and the brain vascular atlas.

4. The method according to claim 1, wherein the vascular image to be studied includes at least one piece of hemodynamic information selected from among: brain vascular volume, Doppler power, flow rate of blood, Doppler color, a value representative of circulation resistance.

5. The method claim 1, wherein the brain vascular atlas contains data stemming from an imaging selected from among ultrasonic imaging, angioscanner, MRI, and a CT scanner.

6. The method according to claim 1, further comprising, between the imaging step and the localization step, a preliminary localization step during which on the vascular image to be studied, at least one characteristic area normally present in any subject to be studied and in the brain vascular atlas is automatically detected, and the vascular image to be studied is thus roughly located in the brain vascular atlas.

7. The method according to claim 6, wherein said characteristic area is selected from among Willis polygon, Sylvian veins, anterior brain artery, and largest arteries of the brain.

8. The method according to claim 1, wherein said brain vascular atlas is produced by vascular ultrasonic imaging of the brain.

9. The method according to claim 1, wherein the reference anatomic atlas is matched with the typical anatomic atlas by shape recognition.

10. The method according to claim 9, wherein a geometrical deformation is determined which gives the possibility of passing from said reference anatomic atlas to the typical anatomic atlas, this geometrical deformation is applied to the brain vascular atlas and the brain vascular atlas is thus matched with the functional areas of the functional anatomic atlas.

11. The method according to claim 1, wherein several initial vascular images are successively carried out by vascular ultrasonic imaging of the brain and several initial anatomic images by said second type of imaging, are successively carried out on several subjects of the class of considered subjects, and said brain vascular atlas and said reference anatomic atlas are determined by a statistical calculation respectively from said initial vascular images and from initial anatomic images.

12. The method according to claim 1, wherein each class of subjects corresponds to at least one criterion selected from among: species, gender, age, and weight.

13. The method according to claim 1, wherein a stimulus is applied to the subject and on the brain vascular image an activation of at least one functional area is detected subsequently to this stimulus.

14. The method according to claim 1, wherein on the brain vascular image, an action targeted towards at least one functional area identified on the brain vascular image is viewed and this action is guided towards said identified functional area.

15. The method according to claim 14, wherein said action is selected from among an electrode implantation, a fluid injection, a remote stimulation with a wave.

16. The method according to claim 1, wherein the imaging step is carried out with at least one ultrasonic probe which is configured to be displaced by a motor-driven unit, and said at least one probe is displaced until the brain vascular image corresponds to at least one desired functional area.

17. The method according to claim 1, wherein the imaging step is carried out with at least one ultrasonic probe adapted for producing a three-dimensional image, and a two-dimensional image corresponding to at least one desired functional area is extracted from this three-dimensional image.

* * * * *